(12) United States Patent
Miljak et al.

(10) Patent No.: US 11,740,191 B2
(45) Date of Patent: Aug. 29, 2023

(54) APPARATUS FOR THE MEASUREMENT OF ORE IN MINE HAUL VEHICLES

(71) Applicant: Commonwealth Scientific and Industrial Research Organisation, Acton (AU)

(72) Inventors: David Miljak, Acton (AU); Richard Yong, Acton (AU)

(73) Assignee: Commonwealth Scientific And Industrial Research Organisation, Acton (AU)

( * ) Notice: Subject to any disclaimer, the term of this patent is extended or adjusted under 35 U.S.C. 154(b) by 0 days.

(21) Appl. No.: 17/788,824

(22) PCT Filed: Dec. 23, 2020

(86) PCT No.: PCT/AU2020/051419
§ 371 (c)(1),
(2) Date: Jun. 24, 2022

(87) PCT Pub. No.: WO2021/127734
PCT Pub. Date: Jul. 1, 2021

(65) Prior Publication Data
US 2023/0038474 A1 Feb. 9, 2023

(30) Foreign Application Priority Data
Dec. 24, 2019 (AU) ................................ 2019904927

(51) Int. Cl.
*G01N 24/08* (2006.01)
*G01R 33/34* (2006.01)
(Continued)

(52) U.S. Cl.
CPC ..... *G01N 24/081* (2013.01); *G01R 33/34007* (2013.01); *G01R 33/441* (2013.01);
(Continued)

(58) Field of Classification Search
CPC .... G01N 24/081; G01N 33/24; G01N 24/085; G01R 33/34007; G01R 33/441;
(Continued)

(56) References Cited

U.S. PATENT DOCUMENTS

2012/0265464 A1 10/2012 Langley
2013/0201481 A1 8/2013 Bamber et al.
(Continued)

FOREIGN PATENT DOCUMENTS

EP 2506040 A1 10/2012
EP 2698214 B1 1/2015
(Continued)

OTHER PUBLICATIONS

Written Opinion of the International Searching Authority dated Feb. 16, 2021 in connection with PCT/AU2020/051419.
(Continued)

*Primary Examiner* — G. M. A Hyder
(74) *Attorney, Agent, or Firm* — Paul Teng

(57) ABSTRACT

Apparatus for the measurement of ore in mine haul vehicles is disclosed, the apparatus comprising: a portal, defining a portal zone, wherein a haul vehicle carrying ore is positionable in or movable through the portal zone; and at least one magnetic resonance (MR) sensor comprised in the portal. The MR sensor includes a main loop and a drive loop located above the main loop. A magnetic resonance sensor control system is provided and configured to control at least one of: the positioning of the at least one MR sensor relative to the portal zone and/or ore burden; the positioning of elements comprised in the MR sensor relative to each other; electromagnetic suppression characteristics of the at least one MR sensor; and/or sensitivity of the at least one MR sensor as a function of distance of the sensor from the ore burden.

28 Claims, 10 Drawing Sheets

(51) Int. Cl.
*G01R 33/44* (2006.01)
*G01R 33/46* (2006.01)
*G01R 33/565* (2006.01)
*G01V 3/175* (2006.01)

(52) U.S. Cl.
CPC ..... *G01R 33/4625* (2013.01); *G01R 33/5659* (2013.01); *G01V 3/175* (2013.01)

(58) Field of Classification Search
CPC ............ G01R 33/4625; G01R 33/5659; G01R 33/341; G01R 33/3628; G01R 33/422; G01R 33/24; G01R 33/4215; G01V 3/175; G01V 3/105; G01V 3/15; G05D 1/0259; G05D 2201/0202; G01S 17/08; G01S 15/08

See application file for complete search history.

(56) References Cited

U.S. PATENT DOCUMENTS

| | | | |
|---|---|---|---|
| 2014/0266196 A1* | 9/2014 | Dai | G01R 33/561 324/309 |
| 2016/0016203 A1 | 1/2016 | Bamber et al. | |
| 2016/0279674 A1 | 9/2016 | Kingman et al. | |
| 2018/0238976 A1* | 8/2018 | Miljak | G01N 24/081 |
| 2020/0164409 A1* | 5/2020 | Shaw | B07C 5/36 |

FOREIGN PATENT DOCUMENTS

| | | |
|---|---|---|
| WO | WO 2011/066600 A1 | 6/2011 |
| WO | WO 2013/078515 A1 | 6/2013 |
| WO | WO 2017/031535 A1 | 3/2017 |
| WO | WO 2017/031537 A1 | 3/2017 |

OTHER PUBLICATIONS

International Search Report dated Feb. 16, 2021 in connection with PCT/AU2020/051419.

International Type Search report dated Jun. 15, 2020 in connection with priority Australian Application No. 2019904927.

Bennett, et al. "The measurement of chalcopyrite in rocks and slurries using magnetic resonance", Mineral Engineering, V22 (2009).

Bennett, et al. "Quantitative Measurement of Copper Mineralogy Using Magnetic Resonance", Mineral Engineering, V20, pp. 1344-1350 (2007).

Bennett, et al. "On-Line Measurement of Mineralogy for Ore Sorting and Characterisation", Applied Mineralogy, ed Pecchio et al. (2004).

Genzhuang, et al. "Development of a bulk ore sorting model for sortability assessment", Minerals Engineering, V141, pp. 1-8 (Jun. 27, 2019).

Coghill, et al. "Consequences of fractal grade distribution for bulk sorting of a copper porphyry deposit", Geoscience Frontiers, V6, pp. 477-480 (2015).

* cited by examiner

APPARATUS FOR THE MEASUREMENT OF ORE IN MINE HAUL VEHICLES

CROSS-REFERENCE TO RELATED APPLICATION

The present application claims priority to Australian provisional patent application no. 2019904927, filed 24 Dec. 2019, the entire content of which is incorporated herein by reference.

TECHNICAL FIELD

The present invention relates to an apparatus and method for measurement of ore on mining trucks and other mobile vehicles used to haul ore.

BACKGROUND

In mining, ore may be extracted underground or in open pits. To physically extract the ore for processing, sections of an ore body are first blasted. The blasted ore, generally having large ore particle topsize (typically up to 1 m), is loaded into haul vehicles using shovels or other loaders. The haul vehicles are used to transport the ore to various possible destinations for continued processing. The destinations may include, for example, a waste dump, a low-grade stockpile, a high-grade stockpile, a leach pad, a primary crusher or a transfer station. The haul vehicles may include, for example, trucks, underground Load Haul Dump (LHD) vehicles or other types of vehicles used to transfer discrete bulk quantities of ore.

The chosen destination of the haul vehicles depends on the characteristics of the ore. An important characteristic is the elemental or mineral grade (concentration) of the ore. For example, ore that has very low grade of the targeted economic minerals may be sent to the waste dump. Alternatively, the grade of other elements or minerals may determine the destination. For example, arsenic is a deleterious element. Ore that is determined to be high in arsenic mineralogy may be diverted to waste or another destination that allows for specialised processing.

Currently, in almost all mining operations, the destination of the haul vehicle is predetermined prior to being loaded with ore. The destination may be determined through analysis of pre-existing data associated with the characteristics of the ore, e.g., as contained in a mine block model. A mine block model is a spatial, discretised representation of ore parameters (such as grade) in the portion of the deposit where mining is planned to occur. In the block model, ore parameters are assigned to individual voxels of ore. The size of each voxel or mine block varies depending on the type of mining and deposit, but a typical size in a large open pit mine may be 10,000 tonnes of ore. The mine block model is generally developed on a statistical basis through analysis of limited ore sample data. Sampling may be provided by mine plan drilling and assay, or mine bench scale sampling and assay. The ore recovery and block model methodology described above is well known in the mining industry.

However, the data relating to each block in the block model is generally only applicable over an entire block size. Depending on the level of grade heterogeneity within a mine block, different sub-lots within the mine block may have ore parameters that vary significantly from the mean block value. Grade estimates associated with lot sizes smaller than the mine block size will have lower confidence levels, to the point that the grade estimates in relatively small ore lots carried by a haul vehicle may have a high uncertainty. Consequently in the general case, the variation in the ore grade at small lot sizes (characterised by the haul vehicle load size), can lead to a misassignment of the destination of the ore. For example, the particular lot of ore in the haul vehicle may correspond to waste grade, yet be sent to a processing destination intended for higher grade ore, based on the mine block data. Such misassignments impact negatively on the mining economics.

There exists an opportunity to improve the mining process by using sensors to measure the grade of elements or minerals in the haul vehicle prior to determining the vehicle destination. By measuring the grade of the actual lot in the haul vehicle, the correct destination can be assigned based on the measurement, thereby leading to an overall reduction in haul vehicle misassignment and an improvement in mine economics. It would therefore be of benefit if the ore mineral grade on trucks could be measured.

Examples of sensing of haul vehicles include applications in uranium and iron ore mining. For example, Srinivas et al.,[1] describes the use of radiometric sensing configured in a portal for detection of uranium progeny isotopes for quantification of uranium grade on a truck. Another known example provided by Temnikov et al.,[2] similarly describes the use of radiometric sensing on mine machinery, including wagons. In other known examples, such as Krukka et al,[3] the use of the Laser Induced Fluorescence (LIF) method is described for detection of phosphorous grade in iron ore, where underground Load Haul Dump (LHD) vehicles were positioned under a LIF sensing station for the purpose of directing the ore destination based on the measurement of phosphorous grade in iron ore.

[1] G. Srinivas et al, "Processor based bulk uranium ore analyser", Proc of the Symposium of advances in nuclear and allied instrumentation, Mumbai India, 5-7 Feb. 1997.
[2] M. A. Temnikov, "Technology of Increasing the quality of uranium ore during extraction and processing", Soviet Atomic Energy, V48 pp153-158 (1980).
[3] A. Krukka et al, "Kiruna mineral processing starts underground: Bulk sorting by LIF", CIM Bulletin, V95, p79, (2002).

The examples given above may be regarded as "portal type" embodiments. Other haul vehicle sensing embodiments (besides portals) are also possible. For example, it is possible to mount sensors in the body of haul vehicles, adjacent to the vehicle ore burden, to measure the haul vehicle ore load.

For reliable determination of haul vehicle ore grade, the measurement must sample a sufficient fraction of the haul vehicle load to provide a representative grade estimate. As ore becomes more heterogeneous, larger fractions of the haul vehicle load must be measured to provide a reliable estimate.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to one aspect of the present disclosure, there is provided an apparatus for the measurement of ore in mine haul vehicles, the apparatus comprising:

a portal, defining a portal zone, wherein a haul vehicle carrying ore is positionable in or movable through the portal zone, at least one magnetic resonance (MR) sensor comprised in the portal, the MR sensor comprising:
a main loop positionable in the portal zone above or on an ore burden carried by the haul vehicle,
a drive loop located above the main loop and electrically isolated from and magnetically coupled to the main loop, wherein a radio frequency (RF) transmitter is couplable to a feed terminal of the drive loop to drive an RF drive current in the drive loop and a radio frequency receiver is couplable to the drive loop to monitor an RF response current in the drive loop;
the apparatus further comprising:
a magnetic resonance sensor control system configured to control at least one of:
the positioning of the at least one MR sensor relative to the portal zone and/or ore burden;
the positioning of elements comprised in the MR sensor relative to each other;
electromagnetic suppression characteristics of the at least one MR sensor; and/or
sensitivity of the at least one MR sensor as a function of distance of the sensor from the ore burden.

In some embodiments, the main loop may comprise a plurality of conductive segments and capacitors positioned between the conductive segments. The capacitors may be evenly spaced along the main loop, and capacitance of each capacitor may be substantially equal. In some embodiments, the capacitance of at least one of the capacitors of the main loop is adjustable. In some embodiments, the sensor control system is configured to adjust the capacitance of at least one of the capacitors of the main loop.

In some embodiments, the apparatus further comprises an impedance monitor to monitor reactive impedance at the feed terminal of the drive loop. The sensor control system may be configured to adjust the capacitance based on the monitored reactive impedance. In some embodiments, the sensor control system may be configured to adjust the capacitance so that the reactive impedance at the feed terminal of the drive loop is at a target reactive impedance.

In some embodiments, the conductive segments and capacitors of the main loop may extend along a looped path and, in cross-section, in a plane perpendicular to the looped path, the conductive segments may have a non-circular cross-sectional shape. In some embodiments, the non-circular shape may be a shape having a convex border and an opposing concave border. The convex border may be at a radially outer side of the main loop and the concave border may be at a radially inner side of the main loop. In some embodiments, the non-circular shape may be a crescent shape, a kidney-shape, or a crescent shape formed by two-intersecting ellipses.

In any of the embodiments discloses herein, the sensor control system may be configured to adjust at least one of: (i) a position and/or orientation of the at least one MR sensor relative to the ore burden; and (ii) a position and/or orientation of the drive loop relative to the main loop. For example, the sensor control system may be configured to control movement of the entire MR sensor, or at least the main loop and drive loop of the MR sensor, so that it is closer to or further from the ore burden. Additionally or alternatively, the sensor control system may be configured to control movement of the main loop and drive loop to be closer together or further apart from each other. To effect movement and changes in orientation, the apparatus may comprise one or more movement actuators, e.g. linear actuators controlled by motors, pneumatics, hydraulics or otherwise.

The apparatus may comprise an impedance monitor to monitor resistive impedance at the feed terminal of the drive loop and the sensor control system may be configured to adjust the position and/or orientation as described above based on the monitored resistive impedance. In some embodiments, the sensor control system may be adapted to adjust the position and/or orientation so that the resistive impedance at the feed terminal of the drive loop is at a target resistive impedance.

In some embodiments, the sensor control system may be configured to adjust the position and/or orientation of the MR sensor relative to the ore burden such that the resistive impedance at the feed terminal of the drive loop is within a predetermined resistive impedance range. In some embodiments, the sensor control system may be configured to subsequently adjust the position and/or orientation of the drive loop relative to the main loop such that the resistive impedance at the feed terminal of the drive loop is at the target resistive impedance.

In some embodiments, the apparatus may further comprise a displacement monitor to monitor a displacement (e.g. changes in position and/or orientation) between the at least one MR sensor and the ore burden. The sensor control system may be configured to adjust the position and/or orientation of the MR sensor based on the monitored displacement. In some embodiments, the sensor control system may adjust the position and/or orientation of the MR sensor based on the monitored displacement to maintain a fixed separation between the ore burden and the main loop.

In any of the embodiments disclosed herein, the apparatus may comprise a reflector positioned above the main loop, the reflector being configured to reduce radiation and magnetic near field in an upward direction from the ore burden.

In any of the embodiments disclosed herein, the apparatus may comprise a passive loop located above or level with (in the plane of) the main loop. The passive loop may be configured to suppress external electromagnetic interface in the main loop.

In some embodiments, the reflector is located between the main loop and the passive loop.

In some embodiments, the passive loop has a capacitive lump impedance that may be adjustable by the sensor control system to optimise suppression of external electromagnetic interface in the main loop.

In embodiments disclosed herein, the apparatus may further comprise a noise monitor to monitor RF noise voltage at the feed terminal of the drive loop. In some embodiments, the sensor control system may be configured to adjust the capacitive lump impedance of the passive loop based on the monitored RF noise voltage to minimise the RF noise voltage at the feed terminal of the drive loop.

In any of the embodiments disclosed herein, the apparatus may further comprise a resistive loop magnetically coupled to the main loop and terminated with a resistance. The sensor control system may be configured to adjust an orientation of the resistive loop relative to the main loop. In some embodiments, the apparatus may comprise an impedance monitor to monitor resistive impedance at the feed terminal of the drive loop and the sensor control system may be configured to adjust the orientation of the resistive loop relative to the main loop based on the monitored resistive impedance, such that the resistive impedance at the feed terminal of the drive loop is at the target resistive impedance.

In embodiments disclosed herein, the apparatus may further comprise an insert that is positioned radially inside of the main loop, in a plane of the main loop. In some embodiments, the insert is an oblate spheroid.

In some embodiments, the haul vehicle is a truck, a Load-Haul-Dump (LHD) vehicle, a skip, a wagon or a cart.

In some embodiments, the measurement of ore may comprise measurement of ore mineral mass and/or ore grade.

In some embodiments, the apparatus comprises a portal control system. The portal control system may be configured to control movement of the haul vehicle through the portal zone of the portal. In some embodiments, the portal control system may be configured to control transfer of information between the apparatus and one or more other components of a mine environment.

In another aspect of the present disclosure, there is provided a method of measuring ore in mine haul vehicles using the apparatus according to any of the embodiments disclosed herein.

As indicated, the sensor control system may be configured to control sensitivity of the at least one MR sensor as a function of distance of the sensor from the ore burden. The sensitivity of the at least one MR sensor may be identified in terms of a "sensitivity profile", being the sensitivity of the at least one MR sensor as a function of distance of the sensor from the ore burden for one or more RF pulse sequences applied to the MR sensor and for one or more associated analysis methods (masks).

Related to this, in some embodiments, apparatuses and methods are disclosed in which one or more predetermined sensitivity profiles are determined for an MR sensor for one or more RF pulse sequences applied to the MR sensor and for one or more associated analysis methods (masks). The masks may be applied to time domain MR signals to preferentially target responses that are diagnostic of different depths of the ore burden. For a particular ore burden to be analysed, weightings may be measured for each of the sensitivity profiles. The one or more sensitivity profile weightings may be used, e.g. by the sensor control system, to estimate the mineral concentration in an ore burden as a function of depth.

For example, in one embodiment, the sensor control system of the apparatus may be configured to:

control application of at least one RF pulse sequence to the MR sensor and use at least one corresponding analysis method to analyse an MR response signal from the ore burden, wherein the at least one RF pulse sequence and its corresponding analysis method have a corresponding predetermined sensitivity profile, use the analysis of the MR response signal to measure a corresponding sensitivity profile weighting; and use the sensitivity profile weighting to estimate the mineral concentration in the ore burden as a function of depth.

In some embodiments, apparatuses and methods are disclosed which utilise or include:

i. determining a first predetermined sensitivity profile for an MR sensor for a first RF pulse sequence applied to the MR sensor and a first associated analysis method (mask);

ii. determining one of more further predetermined sensitivity profiles for the MR sensor for one or more further RF pulse sequence applied to the MR sensor and one or more associated analysis methods (masks);

iii. providing the first RF pulse sequence to the MR sensor and analysing a resulting first MR response signal from an ore burden with the first associated analysis method to measure a first sensitivity profile weighting for the first sensitivity profile;

iv. providing the one or more further RF pulse sequences to the MR sensor and analysing one or more resulting further MR response signals from the ore burden with the one or more further associated analysis methods to measure one or more further sensitivity profile weightings for the one or more further sensitivity profiles;

v. adding the sensitivity profile weightings measured in step (iii) and step (iv) to create a preferred spatial sensitivity profile weighting; and vi. using the preferred spatial sensitivity profile weighting obtained in step (v) to estimate the mineral concentration in the ore burden as a function of depth.

For example, in one embodiment, the sensor control system of the apparatus may be configured to:

control application of a first RF pulse sequence to the MR sensor and use a corresponding first analysis method to analyse a first MR response signal from the ore burden, wherein the first RF pulse sequence and the first corresponding analysis method have a corresponding first predetermined sensitivity profile, control application of one or more further RF pulse sequences to the MR sensor and use one or more corresponding further analysis methods to analyse one or more further MR response signals from the ore burden, wherein the one or more further RF pulse sequences and the one or more further corresponding analysis methods each have corresponding further predetermined sensitivity profiles, use the analysis of the first and further MR response signals to measure corresponding first and further sensitivity profile weightings;

sum the first and further sensitivity profile weightings to create a preferred spatial sensitivity profile weighting; and use the preferred sensitivity profile weighting to estimate the mineral concentration in the ore burden as a function of depth.

Generally, it will be recognised that the sensor control system can comprise a number of control or processing modules for controlling one or more components or functions of the apparatus and may also include one or more storage devices, for storing data, such as predetermined sensitivity profiles, sensitivity profile weightings, impedance values or otherwise. The modules and storage devices can be implemented using one or more processing devices and one or more data storage units, which modules and/or storage devices may be at one location or distributed across multiple locations and interconnected by one or more communication links.

Further, the modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include a non-transitory computer-readable memory medium comprising instructions that cause the processor to perform steps as described herein. The data storage device(s) may include suitable computer readable media such as volatile (e.g., RAM) and/or non-volatile (e.g., ROM, disk) memory or otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments are now described with reference to the accompanying drawings, in which:

FIG. 3b shows a plan view of the magnetic resonance sensor of FIG. 3a;

DESCRIPTION OF EMBODIMENTS

Figure 1:
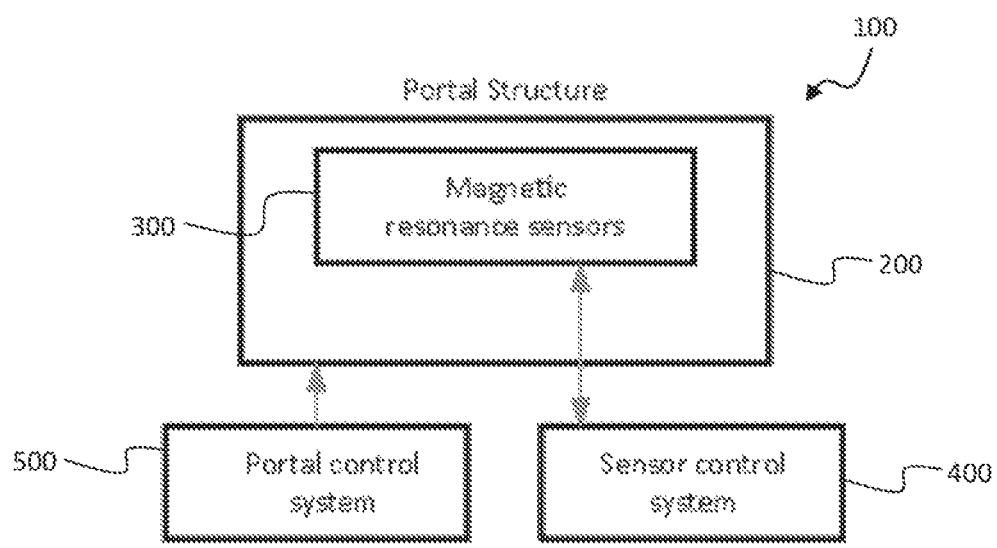
FIG. 1 shows a block component diagram of an apparatus for the measurement of ore in mine haul vehicles according to an embodiment of the present disclosure.

One or more embodiments of the present disclosure may provide, at least in part, an apparatus suitable for measurement of ore while being carried as an ore burden in mine haul vehicles and using magnetic resonance (MR) techniques.

Magnetic resonance is a radiofrequency (RF) spectroscopy used in fields such as fundamental studies of atomic and molecular bonding and routine laboratory characterisation of materials and medical imaging. The majority of applications involve the laboratory use of conventional Nuclear Magnetic Resonance (NMR) for measurements of hydrogen and carbon nuclei to analyse organic compounds. Other less common classes of magnetic resonance include Nuclear Quadrupole Resonance (NQR) and NMR in magnetically ordered materials. These less common classes are applicable to the solid state only, but provide several important measurement advantages. Firstly, in these cases an external static magnetic field need not be applied to define and measure resonances. Secondly, the resonant frequencies are strongly dependent on chemical bonding and crystalline structure and are therefore generally highly specific to a particular crystallographic phase. For the purposes of the specification, "magnetic resonance" refers to these subclasses of NMR, NQR or other related magnetic resonance spectroscopies that do not require the application of an externally applied static magnetic field.

In most types of MR, an RF magnetic field (normally the near field region of an inductive coil or set of coils) is applied to the material to be analysed. In practical terms, the near field region may be defined as the region including both the interior of the inductive sensor and a region surrounding the sensor that extends to a distance equal to several diameters of the sensor.

The measurement sequence in a pulsed MR approach, as can be applied in apparatus according to the present disclosure, involves an excitation phase followed by a detection phase. In the excitation phase, a pulsed RF current is driven in the sensor to illuminate material located in the near field region with RF field. The RF current is driven by a radio frequency transmitter coupled to the sensor. The illumination results in the creation of a dynamic nuclear magnetisation of targeted nuclei in the material, which generates an associated RF response field. The response field may retain significant amplitude after the RF excitation current is switched off.

If the RF response field is generated within the near-field region of a sensor coil (either the same inductive coil used for excitation, or a different coil), then voltages may be produced at output terminals of the sensor which can then be used for detection of the RF response field, using an RF receiver to detect the signal (and noise) voltages at a sensor output terminal. This corresponds to the detection phase of the measurement sequence. The transmitter and receiver are therefore both coupled to the sensor, but typically at different times during the measurement process. The coupling of either the transmitter or receiver to the sensor may be controlled using an RF switch. For detection based on Faraday's Law the terminal voltage is proportional to the time rate change of magnetic flux threading an aperture defined by sensor coil. The magnitude of signal voltages generated in the sensor coil may be used to determine the mass of a specific material within the sensing volume. The determination may be made by application of a simple linear coefficient between the measured signal and the mass within the sensing volume. With auxiliary knowledge of the mass loading inside the sensing volume, the concentration of the material and grade may also be determined.

For example, the mineral mass M may be calculated according to:

$$M = a \times S$$

where a is a calibration factor, and S a magnetic resonance signal voltage.

The grade G may calculated according to:

$$G = b \times \frac{M}{M_o}$$

where b is a fixed calibration factor and $M_o$ is an estimate of the mass of ore in a sensing zone. $M_o$ may be assumed to be a fixed value, or a value determined through measurement of the ore profile carried on the haul vehicle.

Known applications using MR techniques typically involve measurement of relatively small samples (e.g., less than 1 L in sample volume), and are performed in controlled environments, such as completely electromagnetically shielded sensors, or in Magnetic Resonance Imaging (MRI) installations that are also completely shielded. In this regard, electro-magnetic (EM) shielding is required to avoid poor signal to noise ratio due to external electromagnetic disturbances interfering with the detection of the MR signal.

Figure 2:
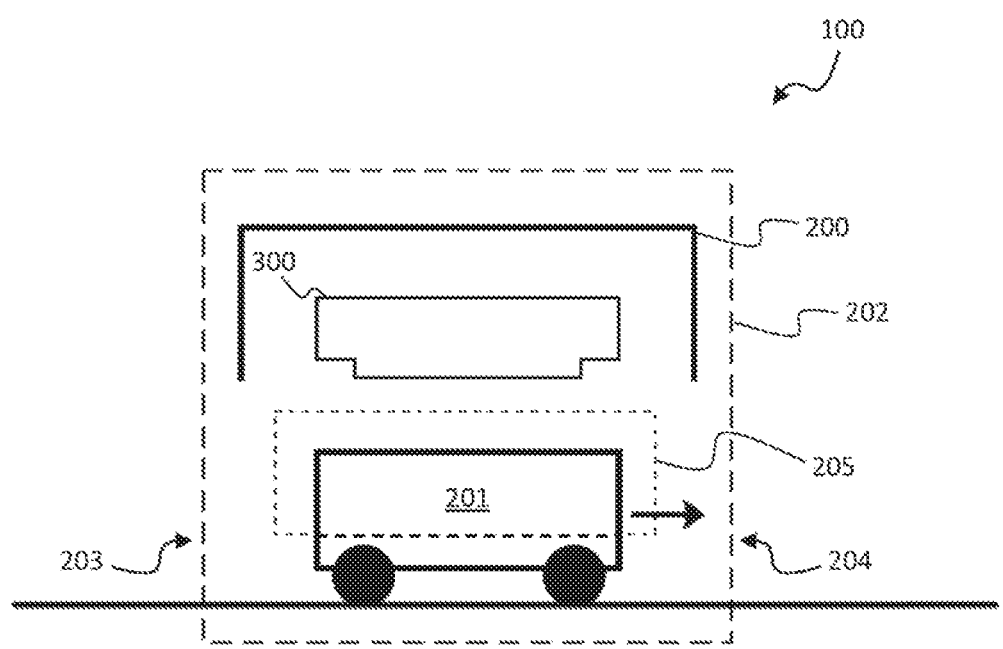
FIG. 2 shows a side schematic view of an apparatus for the measurement of ore in mine haul vehicles according to an embodiment of the present disclosure.

FIG. 1 illustrates an apparatus 100 for the measurement of ore in mine haul vehicles 201 according to an embodiment of the present disclosure. The apparatus 100 comprises a portal 200, at least one magnetic resonance (MR) sensor 300 comprised in the portal 200, a magnetic resonance sensor control system 400 and optionally a portal control system 500. Referring to FIG. 2, the portal defines a portal zone 202. The portal 200 is a mechanical structure, e.g. having a frame, that can accommodate both the mechanical integration of the at least one magnetic resonance sensor 300, and the passage of a haul vehicle 201 through or at least adjacent that portal 200, as illustrated in FIG. 2, while the haul vehicle 201 is carrying ore material (an ore burden).

The sensor control system 400 is generally configured to control features of the apparatus to assist in the magnetic resonance sensor's ability to work in a portal environment and/or to provide for more reliable or accurate measurements using the magnetic resonance sensor 300. The sensor control system 400 may control, for example, at least one of: the positioning of the at least one MR sensor 300 relative to a zone of the portal 200 and/or relative to the ore burden; the positioning of elements comprised in the MR sensor 300 relative to each other; electromagnetic suppression characteristics of the at least one magnetic resonance sensor 300; and/or sensitivity of the at least one magnetic resonance sensor 300 as a function of distance of the sensor 300 from the ore burden.

The portal control system 500 may control, for example, at least one of: movement of the haul vehicle 201 through the portal zone 202 of the portal 200 (e.g. stopping and starting of movement); and transfer of information between the apparatus 100 and one or more other components of a mine environment. In practice, the sensor control system 400 and the portal control system 500 may be integrated into a broader control system for the apparatus, or kept as separate control system elements.

The portal 200 has physical dimensions that define the volume or area of the portal zone 202. Preferably, the portal zone 202 is of sufficient size so as to accommodate commonly used haul vehicles 201 while carrying ore burdens. In some embodiments, the portal 200 may be adapted to allow or cause transport of a haul vehicle 201 from an entry 203 of the portal zone 202 to an exit 204 of the portal zone, thereby defining a haul vehicle transport path, i.e., entry 203 to exit 204.

In some embodiments, the haul vehicle 201 carrying ore material may continuously move through the portal zone 202 along the vehicle transport path. Alternatively, or in addition to, the haul vehicle 201 may stop at a specified position within the portal zone 202. In this manner, the haul vehicle 201 may be stationary and/or moving during a measurement of the ore material carried on the haul vehicle 201. The apparatus 100 may include a conveyor or other traction system to move the haul vehicle 201, with the movement of the haul vehicle 201 by the conveyor being controlled by the portal control system 500. Alternatively, the haul vehicles may be self-propelled through the portal zone or moved by other means.

In general, the apparatus 100, including the portal 200 and/or portal zone 202, may be adapted to measure ore carried by a variety of different haul vehicles, including those that are capable of self-propulsion such as a truck, a train, or a Load-Haul-Dump (LHD) vehicle, or a skip, a wagon, or a cart, or similar, which may be positioned within the portal zone 202 for ore measurement and moved by the apparatus 100 or other means.

Haul vehicles may carry loads spanning between several tonnes and up to 350 tonnes, for example. In order to make a representative measurement of ore material, potentially large ore volumes (e.g., many cubic metres) may need to be measured. The magnetic resonant (MR) frequencies associated with selected/target mineral phases generally sit below 100 MHz. At such frequencies the electromagnetic skin depth of rock types such as granite is typically at least several metres. Therefore, magnetic resonance techniques according to the present disclosure may provide for bulk measurement of ore carried by haul vehicles.

For large volume, bulk, measurements, the ore burden can be approximated as an ore-half-space.

In order to optimise the detection of ore at large distances from the sensor or otherwise, aspects of the apparatus including the at least one MR sensor of the apparatus 100 may be optimised, potentially in combination.

For instance, the apparatus 100 may be configured so that the radio frequency (RF) field at large distances from the MR sensor 300 can be maximised using the available radio frequency power. Below a certain field strength threshold, the induced response field decreases exponentially. Increased RF field strength at depth enables an increase in the sensed volume of the ore burden.

Moreover, the MR sensor 300 may be configured to account for electrical impedance changes associated with proximity of ore and other machinery.

In addition, the MR sensor 300 may be configured to reject potentially high levels of external electromagnetic interference. For measurement of ore burden carried by a haul vehicle using a portal structure, it may be impractical to completely shield the haul vehicle during the measurement, e.g. due to the requirement of portal entry and exit points. At best, only partial shielding may be applied. The measuring of ore carried by haul vehicles using a portal arrangement can be considered an "open system", where complete electromagnetic (EM) shielding techniques/equipment may not be applicable and therefore other means to reject electromagnetic interference may be particularly advantageous.

It may also be advantageous that the MR sensor 300 is configured to return a uniformly weighted measurement of the ore burden carried by a haul vehicle in the portal zone 202. That is, in some embodiments it is preferable that the MR sensor 300 is not overly sensitive to inhomogeneous mineral or elemental grade distributions. For example, this may apply in situations where high grade ore material very close to the sensor results in an overestimate of total grade due to the fact that the sensor sensitivity is stronger in the spatial zone closer to the MR sensor 300.

As discussed in more detail in Example 4 below, different configurations of pulse sequences applied to the MR sensor 300 may modify the characteristics of the spatial sensitivity of the MR sensor 300 in the measurement zone 205 (the ore half space). In embodiments of the present disclosure, pulse sequences, and signal analysis methods, may be modified to preferentially suppress the sensitivity of the MR sensor 300 at regions very close to (e.g., adjacent) the MR sensor 300, while leaving the sensitivity far from the MR sensor 300 relatively unaffected.

One or more predetermined sensitivity profiles may be determined for the MR sensor 300 for one or more RF pulse sequences applied to the MR sensor 300 and for one or more associated analysis methods (masks). The masks may be applied to time domain MR signals to preferentially target responses that are diagnostic of different depths of the ore burden. For a particular ore burden to be analysed, weightings may be measured for each of the sensitivity profiles. The one or more sensitivity profile weightings may be used to estimate the mineral concentration in an ore burden as a function of depth.

In one embodiment, the sensor control system 400 of the apparatus 100 is configured to:

control application of at least one RF pulse sequence to the MR sensor 300 and use at least one corresponding analysis method to analyse an MR response signal from the ore burden, wherein the at least one RF pulse sequence and the at least one corresponding analysis method each have a corresponding predetermined sensitivity profile, use the analysis of the MR response signal to measure a corresponding sensitivity profile weighting; and use the sensitivity profile weighting to estimate the mineral concentration in the ore burden as a function of depth.

In some embodiments, e.g., in accordance with an approach described in more detail in Example 4, the apparatus or an associated method for the measurement of ore, including e.g., measurement of mineral concentration or grade, may utilise or include:

i. determining a first predetermined sensitivity profiles for the MR sensor 300 for a first RF pulse sequence applied to the MR sensor 300 and a first associated analysis method (mask);

ii. determining one of more further predetermined sensitivity profiles for the MR sensor 300 for one or more further RF pulse sequence applied to the MR sensor 300 and one or more associated analysis methods (masks);

iii. providing the first RF pulse sequence to the MR sensor 300 and analysing a resulting MR response signal from an ore burden with the first associated analysis method to measure a first sensitivity profile weighting for the first sensitivity profile;

iv. providing the one or more further RF pulse sequences to the MR sensor 300 and analysing one or more resulting MR response signals from the ore burden with the one or more further associated analysis method to measure one or more further sensitivity profile weightings for the one or more further sensitivity profiles;

v. adding the sensitivity profile weightings measured in step (iii) and step (iv) to create a preferred spatial sensitivity profile weighting; and vi. using the preferred spatial sensitivity profile weighting obtained in step (v) to estimate the mineral concentration in the ore burden as a function of depth.

For example, in one embodiment, the sensor control system 400 of the apparatus 100 is configured to:

control application of a first RF pulse sequence to the MR sensor 300 and use a corresponding first analysis method to analyse a first MR response signal from the ore burden, wherein the first RF pulse sequence and the first corresponding analysis method have a corresponding first predetermined sensitivity profile, control application of one or more further RF pulse sequences to the MR sensor 300 and use one or more corresponding further analysis methods to analyse one or more further MR response signals from the ore burden, wherein the one or more further RF pulse sequences and the one or more further corresponding analysis methods each have corresponding further predetermined sensitivity profiles, use the analysis of the first and further MR response signals to measure corresponding first and further sensitivity profile weightings;

sum the first and further sensitivity profile weightings to create a preferred spatial sensitivity profile weighting; and use the preferred sensitivity profile weighting to estimate the mineral concentration in the ore burden as a function of depth.

Figure 3A:
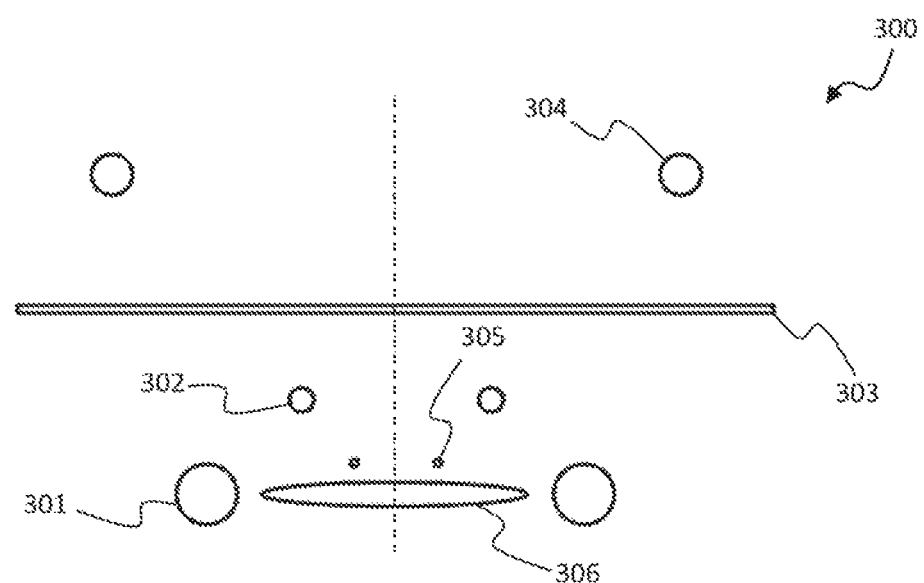
FIG. 3a shows a cross-sectional view of a magnetic resonance sensor according to an embodiment of the present disclosure.

The at least one MR sensor 300 according to an embodiment of the present disclosure is now described in more detail with reference to FIGS. 3a and 3b. As shown in FIG. 3a, the magnetic resonance sensor 300 comprises a main loop 301 positionable above the ore burden or resting on top of the ore burden of a haul vehicle 201, and a secondary loop (drive loop 302) positioned coaxially with, and above the plane of, the main loop 301. The drive loop 302 is electrically isolated from, and magnetically coupled to, the main loop 301, and series resonated at an appropriate frequency. The main loop 301 is resonated at a series resonance frequency substantially the same as the drive loop resonance frequency (typically within 2%).

The drive loop 301 is fed by a radiofrequency (RF) transmitter at a drive loop feed terminal 3013. An RF drive current in the drive loop 302 excites an RF drive current in the main loop 301, generating an RF magnetic field in a measurement zone 205 of the apparatus 100, the RF magnetic field being suitable for changing the magnetisation of target nuclei in the ore carried by the haul vehicle 201. In general, the measurement zone will intersect, at least in part, with the vehicle transport pathway of the haul vehicle 201. A RF response current is excited in the main loop 301 by precession of the magnetisation of the target nuclei, and the RF response current in the main loop 301 causes a corresponding RF response current in the drive loop 302 that is monitored by a radio frequency receiver (not shown) coupled to the drive loop 302.

The main loop 301 of the at least one magnetic resonance sensor 300 is adapted to have a series resonance frequency, and the at least one magnetic resonance sensor is adapted to have an associated operating frequency, suitable for magnetic resonance measurements of a target nuclei. It will be appreciated by the person skilled in the art that the resonant absorption and emission of energy by the ensemble of target nuclei may have a frequency distribution. The peak magnetic resonance frequency is defined as the mode of the frequency distribution. The operating frequency of the at least one magnetic resonance sensor 300 may be suitable for magnetic resonance measurements of the target nuclei when the series resonance frequency is close to the peak magnetic resonance frequency.

Setting the operating frequency close to the peak resonance frequency of the target nuclei improves the sensitivity of the magnetic resonance sensor 300 to small amounts of target nuclei by enabling a greater RF signal current to be excited in the main loop 301. For example, the operating frequency may be set such that the frequency of the excited RF current is within two standard deviations (of the magnetic resonance frequency distribution of the target nuclei) from the peak magnetic resonance frequency of the target nuclei.

Figure 3B:
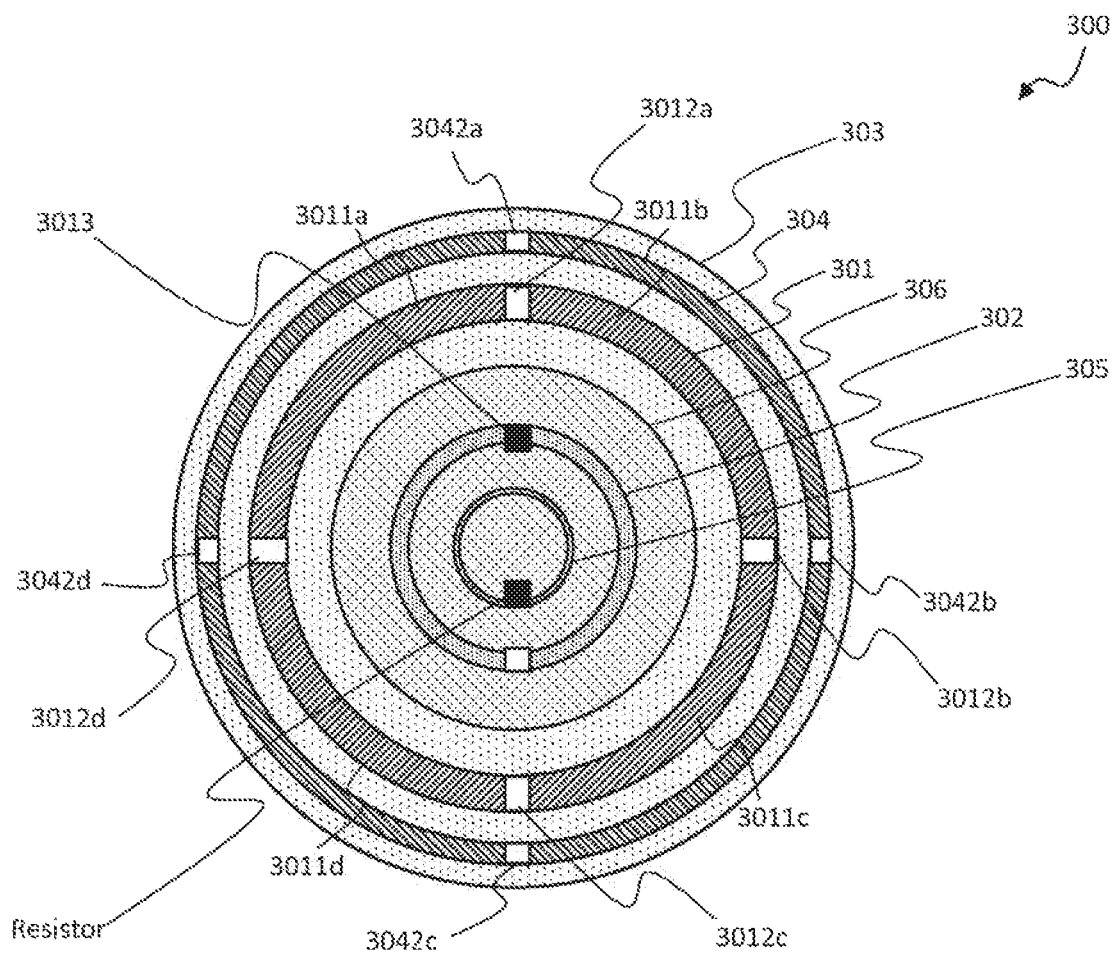

Turning attention specifically to the main loop 301, and with reference to FIGS. 3a and 3b, the main loop 301 is a planar loop (e.g., single turned coil) positioned above the ore burden, or resting on top of the ore burden, of a haul mine vehicle 201. The main loop 301 conducts the RF electrical current so that it is predominantly in-phase over the entire main loop. The RF current generates an RF magnetic field suitable for changing the magnetisation of target nuclei; such as, by resonantly exciting the target nuclei to change the orientation of the net magnetisation of the ensemble of target nuclei. Also, the main loop 301 is adapted to have an RF signal current excited by precession of the magnetisation of the target nuclei in the ore material being analysed.

The main loop 301 is partitioned into discrete multiple conductive sections 3011a-d separated by tuning capacitors 3012a-d. The capacitance of the tuning capacitors 3012a-d are approximately equal (e.g., to within 10% of each other) and chosen to series resonate the main loop 301. The partitioning into the sections 3011a-d is made to achieve an approximately uniform RF current in the main loop 301. A uniform RF current optimises the near field homogeneity in the illuminated half space of the ore burden. The partitioning also minimises the maximum electrical voltage at points on the main loop 301, due to electric charge non-uniform distribution, with respect to ore or other elements in the near-field region (i.e., near zone) of the electromagnetic field (EM) of the main loop 301. This reduces the RF loss mechanisms associated with non-uniform loop charge distribution, lowering the main loop resistance and allows an increase of RF field magnitude in the near-field region.

In some embodiments, at least one of the tuning capacitors 3011a-d is adjustable so as to allow modification of the series resonance of the main loop 301.

It is advantageous that the inductance of the main loop 301 be minimised, but without compromising the field generation in the measurement zone 205. A quality factor of the loop is defined as the loop reactance divided by the loop resistance. At a fixed quality factor of the loop, a minimum inductance implies a corresponding minimum in loop resistance. In general, the main loop 301 can be considered to extend along a looped path.

In some embodiments, the cross-section of the main loop 301 (in a plane perpendicular to the looped path) may be circular in shape, providing the main loop 301 with a substantially toroidal overall shape. In the present disclosure, however, it has been advantageously recognised that differently shaped (non-circular) cross sections for the main loop may also be utilised, e.g. in order to minimise the inductance of the main loop 301.

Shaping of the main loop cross section can reduce the inductance compared to a circular cross section of a toroid. FIG. 5c shows a comparison of the field per unit current generated by a main loop with different cross-sectional shapes, with the constraint that the shapes have the same vertical dimensions (by maintaining the same vertical dimensions, differences in field per unit current can be recognised based on the change in shape only, rather than due to modification of distances between the main loop and the ore). In FIG. 5c, two traces are provided, one trace being the normalised on-axis field obtained from a circular cross-sectional/toroidal shaped main loop (of FIG. 5a), and the other trace being the normalised on-axis field obtained using a non-circular shaped main loop (of FIG. 5b). The field generated by the main loop is virtually identical for each case. However there is a significant difference in the loop inductance for each case, as seen in Table 1 below. The non-circular cross-sectional shape, despite having the same vertical dimension and on-axis normalised field distribution as the conventional circular shape, has 20% lower inductance. The non-circular cross-sectional shape is therefore advantageous for reducing the sensor inductance and resistance.

TABLE 1

Figure 5A:
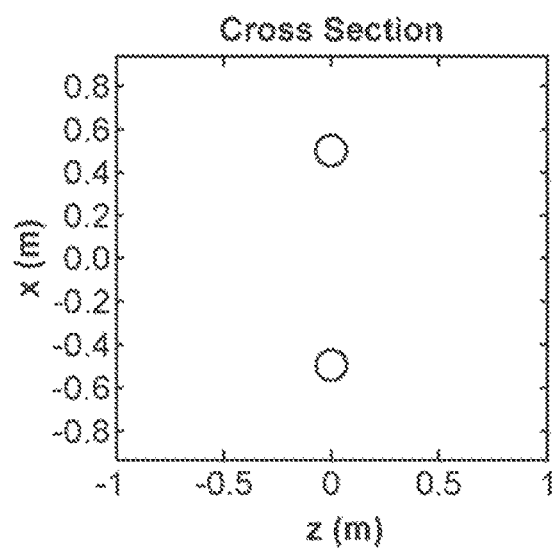
FIG. 5c shows normalised on-axis fields per unit current for a main loop with a circular cross-section (FIG. 5a) and non-circular cross section (FIG. 5b)

Loop inductance for the loop cross-section geometries shown in FIGS. 5a & and 5b

| Cross section | Inductance (µH) |
|---|---|
| Circular | 1.26 |
| Non-circular | 1.05 |

Figure 5B:
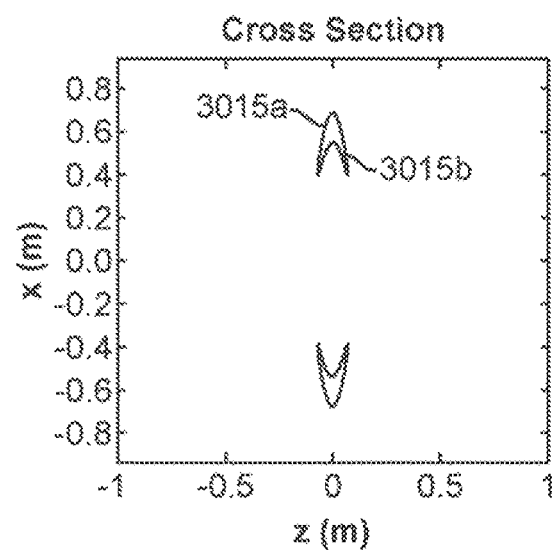
Figure 5C:
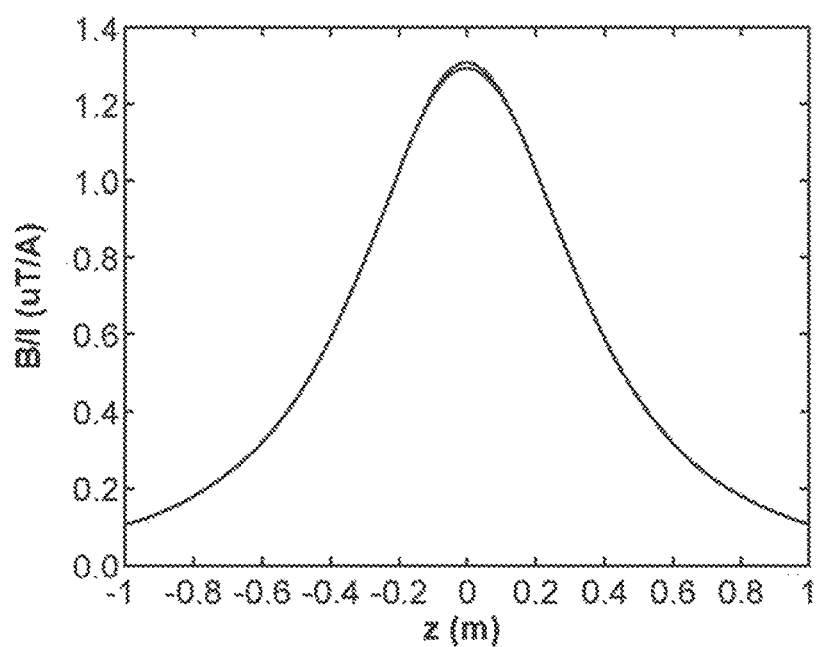

As seen in FIG. 5b, the non-circular shape is a shape having a convex border 3015a and an opposing concave border 3015b. The convex border 3015a is at a radially outer side of the main loop and the concave border 3015b is at a radially inner side of the main loop. The non-circular shape may be considered kidney-shaped, crescent-shaped, or of a crescent shape formed by two-intersecting ellipses. Other non-circular shapes are possible.

Now turning to the drive loop 302, the drive loop 302 is series resonated using a plurality of capacitors 3022a-d at the operating frequency and is magnetically coupled to the main loop 301. The mutual coupling of the drive loop 302 and the main loop 301 is adjustable by varying the position of the drive loop 302 with respect to the main loop 301. The variable position allows modification of the real part of the input electrical impedance at the feed terminal 3013. This can account for variable electrical impedance imparted by variable ore burden presentations on the haul vehicle 201.

Figure 4:
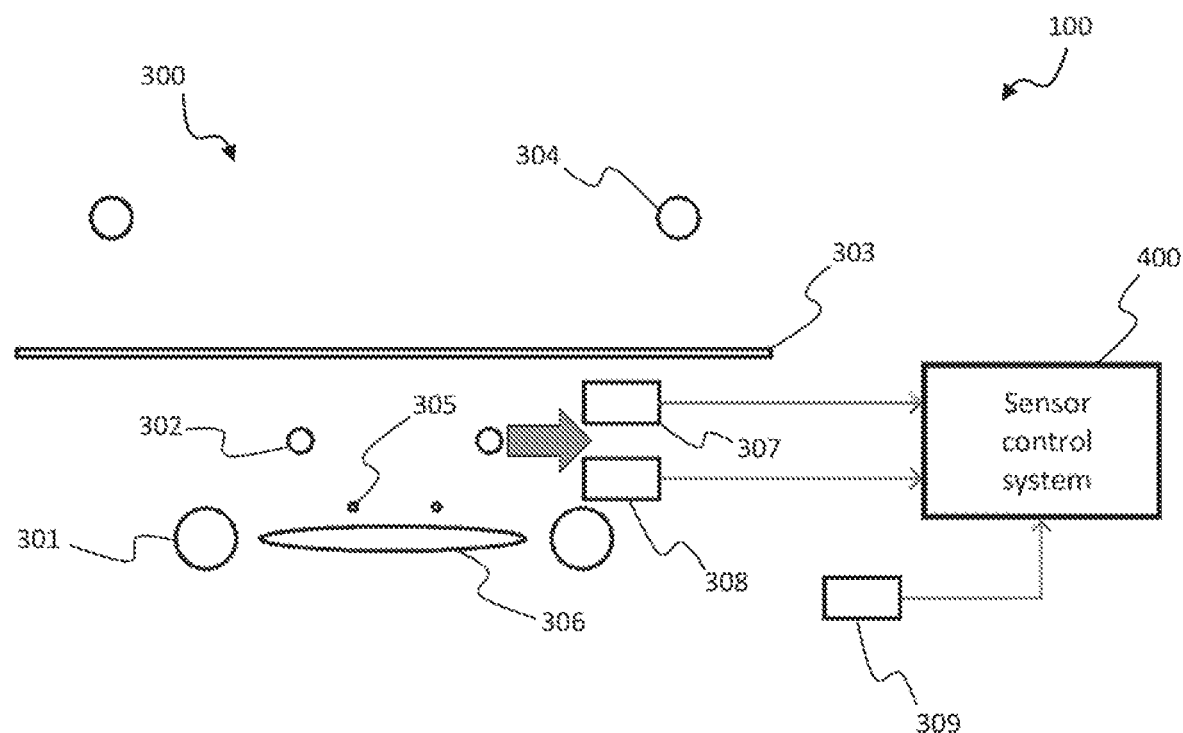
FIG. 4 shows a schematic view of a magnetic resonance sensor and sensor control system according to an embodiment of the present disclosure.

With reference to FIG. 4, the apparatus may comprise at least one impedance monitor 307 and an RF receiver 308. The impedance monitor 307 may monitor reactive and/or resistive impedance at the feed terminal of the drive loop 302 and provide details of the monitored impedance to the sensor control system 400. The RF receiver 308 may detect the signal (and noise) voltages during the detection phase of the measurement sequence.

In some embodiments, the sensor control system 400 is configured to adjust the capacitance of at least one of the capacitors of the main loop 301, e.g. based on the monitored reactive impedance. This may be carried out so that the reactive impedance at the feed terminal of the drive loop 302 is adjusted to a target reactive impedance. The targeted feed terminal reactive impedance is typically close to zero var-ohm.

In some embodiments, as shown in FIG. 4, the sensor control system 400 comprises a displacement monitor 309 to monitor a position, orientation and/or displacement between the at least one MR sensor 300 and the ore burden. In these embodiments, the sensor control system 400 adjusts the position and/or orientation based on the monitored displacement. The sensor control system 400 may adjust the position and/or orientation based on the monitored displacement to maintain a fixed separation between the ore burden and the main loop 301 of the MR sensor 300.

In some embodiments, the sensor control system 400 is configured to control a position and/or orientation of the at least one MR sensor 300 relative to the ore burden. Alternatively, or in addition to, the sensor control system 400 may be configured to control a position and/or orientation of the drive loop 302 relative to the main loop 301. In some embodiments, the sensor control system adjusts the position and/or orientation based on the monitored resistive impedance. In some embodiments, the sensor control system 400 adjusts the position and/or orientation of the at least one MR sensor 300 relative to the ore burden such that the resistive impedance at the feed terminal of the drive loop 302 is within a predetermined resistive impedance range. This resistive impedance range may be typically be within 30% of the target feed terminal resistive impedance. Subsequently, the sensor control system 400 may adjust the position and/or orientation of the drive loop relative to the main loop such that the resistive impedance at the feed terminal of the drive loop is at the target resistive impedance. The target resistive impedance is a fixed system impedance that is predetermined and selected for optimisation of RF power transfer from the transmitter to the sensor. A typical target resistive impedance is 50 ohms.

It is advantageous to maintain a fixed and optimised electrical impedance at the (high power) drive loop feed terminal 3013. The position of the drive loop 302 can be set according to a measurement of the difference between the drive loop feed terminal input impedance and the targeted input impedance. The position of the drive loop 302 may be varied according to a vertical displacement or an angular displacement.

It will be appreciated by the skilled addressee that the at least one MR sensor 300 may comprise other conducting elements, impedance monitors, actuators, combination loops, inserts, reflectors, drive coils, and/or other reflectors/shields.

Figure 3C:
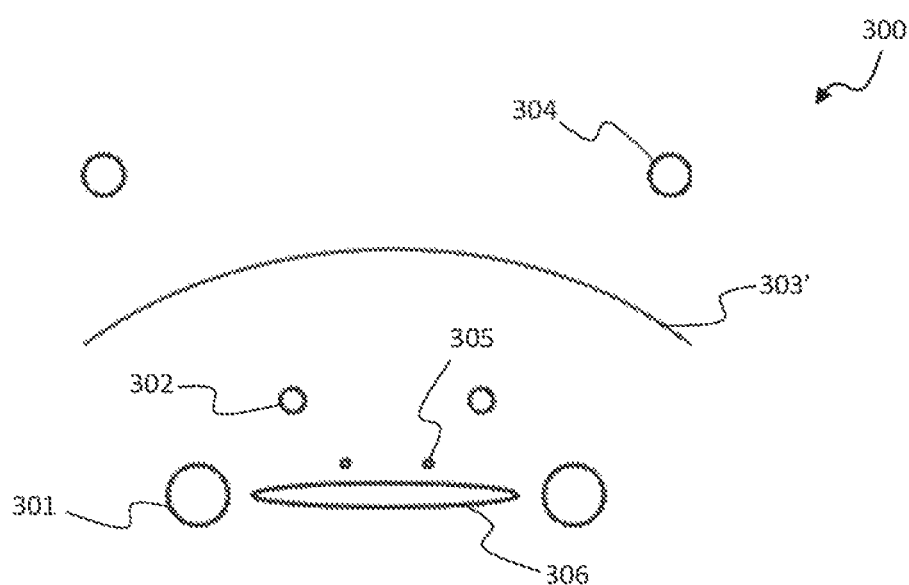
FIG. 3c shows a cross-sectional view of a magnetic resonance sensor according to an embodiment of the present disclosure.

With reference to FIG. 3a, in some embodiments the at least one magnetic resonance sensor 300 further comprises a passive reflector 303, which may be coaxial with the main loop 301, and positioned above the main loop 301 and the drive loop 302. In preferred embodiments, the reflector 303 is configured (e.g., positioned) to reduce the radiation and magnetic near field into the direction opposite the measurement zone 205 (i.e., opposite the ore half space). In some embodiments, the reflector is configured to reduce radiation and magnetic near field in an upward direction from the ore burden. In some embodiments, as illustrated in FIG. 3a, the reflector 303 may be a substantially flat, disc shaped structure, having no aperture. In alternative embodiments, as illustrated in FIG. 3c, the reflector 303' may be a dome-shaped structure, having no aperture. For the case of a dome shaped reflector 303' structure, the concave side of the dome faces the main loop 301.

Still referring to FIG. 3a, in some embodiments, the at least one magnetic resonance sensor 300 may comprise a passive loop 304 (a single turn coil) positioned coaxial with the main loop 301, and either above the main loop 301 as shown in FIG. 3a, or else in the plane of the main loop 301. The passive loop 304 is magnetically coupled to the main loop 301. The passive loop 304 has a specifically selected capacitive lump impedance inserted in series so as to provide suppression of external electromagnetic interference in the main loop 301. In some embodiments, the specific capacitive lump impedance is varied, e.g. by the sensor control system 400, in order to optimise the suppression of external electromagnetic interference/minimise RF noise voltage, based on a measurement of the RF noise voltage at the drive loop feed terminal. The at least one MR sensor 300 may comprise a noise monitor to monitor RF noise voltage at the feed terminal of the drive loop 302. The RF receiver may act as the noise monitor.

In some embodiments, the reflector 303 is located between the main loop 301 and the passive loop 304. In this regard, the reflector 303 may play a role in reducing a mutual coupling between the main loop and a passive loop 304, as discussed in more detail in Example 2 below.

In some embodiments, and illustrated in the embodiment of FIG. 3a, the at least one MR sensor 300 comprises a resistive loop 305 magnetically coupled to the main loop 301, and terminated with a resistance. The orientation of the resistive loop 305 can be modified with respect to the main loop 301 to impart variation in the resistive impedance of the drive loop feed network. The resistive loop 305 may be used to modify the overall resistive losses in the magnetic resonance sensor 300, in order to control the RF current in the main loop 301.

In some embodiments, the sensor control system 400 is configured to adjust an orientation of the resistive loop 305 relative to the main loop 301. In these embodiments, the apparatus 100 may comprise an impedance monitor to monitor resistive impedance at the feed terminal of the drive loop 302, and the sensor control system 400 may be configured to adjust the orientation of the resistive loop 305 relative to the main loop 301 based on the monitored resistive impedance. In this manner, the resistive impedance at the feed terminal of the drive loop 302 can be placed or maintained at a target resistive impedance.

Still referring to FIG. 3a, in some embodiments the at least one magnetic resonance sensor 300 comprises a passive insert 306 positioned in the plane of the main loop 301, and inside the minimum radius of the main loop 301. The passive insert 306 may be a disc, or ellipsoid structure, having no aperture. In some embodiments, the passive insert 306 is an oblate spheroid. The outer surface of the insert may be composed of material with high electrical conductivity, such as copper. An inner portion of the insert may be composed of the same material as the outer surface or otherwise.

In accordance with the present disclosure, the passive insert 306 may be used to suppress RF field immediately adjacent to the main loop 301, but configured to minimally affect the RF field at a larger distance from the main loop 301. Therefore, the passive insert 306 may act to suppress eddy currents in the measurement zone 205 (i.e., the ore half space) immediately adjacent to the main loop 301, in order to reduce the effective resistance of the main loop. This configuration may thereby increase the current in the main loop 301 and provide for an overall increase in the RF field at positions distant from the main loop 301.

Another advantageous effect of the passive insert 306 may also be to flatten the MR sensitivity profile in the measurement zone 205 (i.e., the ore half space) by reducing the local sensitivity for positions very close to the sensor.

Figure 6:
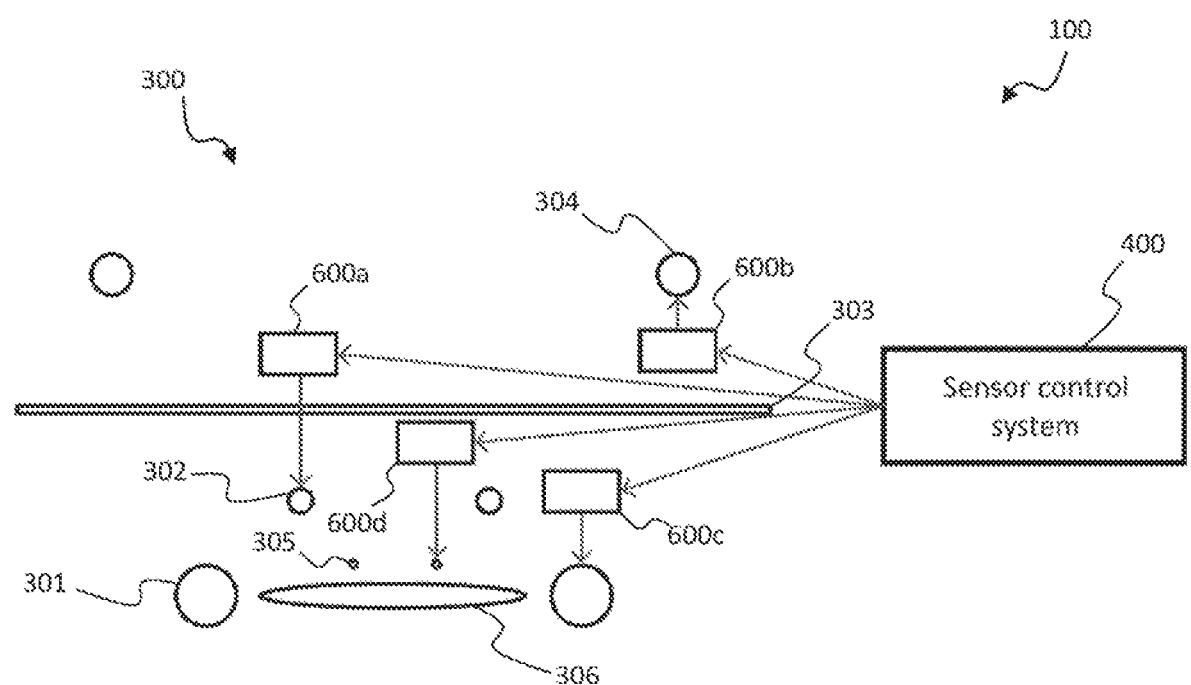
FIG. 6 shows a schematic view of a magnetic resonance sensor and sensor control system according to an embodiment of the present disclosure.

With reference to FIG. 6, the control system 400 may include actuators (600a-d) to modify the position and/or orientation of the magnetic resonance sensor 300 and elements within the magnetic resonance sensor 300 including the main loop 301, drive loop 302, passive loop 304, and resistive loop 305. The sensor control system can use measured information for this purpose, including the complex impedance of the sensor drive loop feed terminal, the noise voltage at the sensor drive loop feed terminal (e.g., as measured by a radio frequency receiver), and the distance between a sensor front face and the ore carried in the haul vehicle (e.g., by means of ultrasonic or laser distance measurement methods).

Example 1—Passive Loop ("Gradiometer") Function

Figure 7:
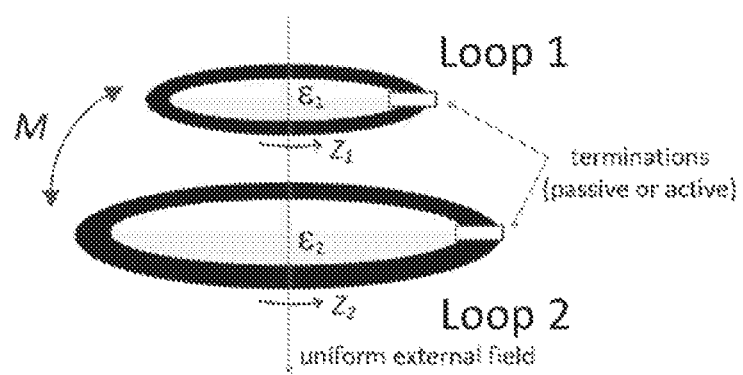
FIG. 7 illustrates functionality of loops forming an RF gradiometer according to an embodiment of the present disclosure.

With reference to FIG. 7, when two loops ("loop 1" and "loop 2") are immersed in a uniform interfering magnetic field the structure of the scattered field may be used to provide a level of RF interference suppression in one of the loops. An analysis may begin by assuming that the external interfering field contributes electromotive forces $\varepsilon_1$ and $\varepsilon_2$ to loop 1 and loop 2 respectively. The electromotive forces will be proportional to the respective loop areas. In this analysis loop 1 may be identified as the "main loop" and loop 2 as the "passive loop", e.g. in accordance with preceding embodiments. A bowl shaped or disc-shaped "passive reflector" e.g. in accordance with preceding embodiments, and to be discussed further, may be interposed between loop 1 and loop 2, but is omitted from analysis for now. It is further assumed that $\varepsilon_1$ and $\varepsilon_2$ are in phase. This normally implies that the loops are separated by a distance much less than a free space wavelength and couple to the same field polarisation. The ratio $\alpha = \varepsilon_2/\varepsilon_1$ is therefore a positive real number. The loops are also assumed to be physically small compared to the free space wavelength. It then follows that the principle of lumped circuit analysis may be used to analyse the electromotive forces in each loop due to the external field and the scattered field from the other loop.

Each loop, when completely isolated from the other (mutual inductance M=0), has a generally complex loop impedance taken in series around the loop path of $Z_1 = r_1 + jX_1$ and $Z_2 = r_2 + jX_2$. These impedances encapsulate internal loop resistance and inductance, and external inductance. They also include any terminating impedances loading the loops, in the form of tuning elements and, in the case of loop 1, the input impedance of a receiver present during the reception phase of the measurement. When M≠0 it can be shown that the total electromotive force CT in loop 1 is $$\varepsilon_T = \varepsilon_1 \frac{(1+\gamma^2 + \alpha\beta + j\alpha\beta\gamma)}{(1+\gamma^2)D}, \quad D = 1 + \frac{\omega^2 M^2}{Z_1 Z_2}, \quad (1)$$

where $\beta = \omega M/X_2$, $\gamma = r_2/X_2$. We seek a combination of parameters that minimises $|\varepsilon_T|/|\varepsilon_1|$. To proceed, it is noted that the magnitude of the numerator in (1) can be minimised by judicious choice of M and loop 2 termination:

$$\frac{\alpha\beta}{1+\gamma^2} = -1, \text{ or } X_2 \approx -\alpha\omega M, \quad (2)$$

where the approximation for $X_2$ is valid for small $|\gamma|$ and $\alpha\omega M > 2r_2$. This particular choice for $X_2$ yields:

$$\frac{|\varepsilon_T|}{|\varepsilon_1|} = \frac{|\gamma|}{|D|}. \quad (3)$$

It is observed that, by taking small $|\gamma|$, a potentially large reduction in $|\varepsilon_T|$ may be obtained. It must be verified that D is also not small. D may be recast as follows:

$$D = \frac{\left(1+\gamma^2+\frac{\beta^2 r_2}{Z_1}\right) - j\frac{\beta^2 r_2}{\gamma Z_1}}{(1+\gamma^2)}. \quad (4)$$

To make further progress, we note that loop 1 would normally operate very close to resonance with $Z_1$ essentially purely real ($X_1$=0), in order to achieve efficient RF power coupling during the excitation phase of the measurement. Under this assumption $|D|>1$ always.

As an example, the following parameters may be (independently) selected: $\alpha=2$, $r_2/r_1=2$, $|\gamma|=0.1$. Then $\beta \sim -0.5$ and $|D|=5.1$. For these parameters the correct phasing of the scattered field is achieved and the RFI reduction factor according to Equation (3) is 0.019 or 34 dB.

Finally, we may check the impedance $Z_T$ "seen" by a test voltage applied in series with loop 1 (where equation (2) simultaneously applies), which takes account of the reflected impedance of loop 2, as this is the pertinent impedance relating to current drive in loop 1:

$$Z_T = Z_1' + \frac{\omega^2 M^2}{Z_2} = \left(r_1' + r_2\frac{\beta^2}{1+\gamma^2}\right) + j\left(X_1' - \frac{\beta^2 r_2}{\gamma(1+\gamma^2)}\right), \quad (5)$$

where $Z_1' = r_1' + jX_1'$ is the impedance of loop 1 when completely isolated, but with receiver circuitry not contributing to the loading of the loop. In practice $Z_1'$ is usually similar to $Z_1$. It is noted that under the chosen parameters the resistance (real part of $Z_T$) has only a small contribution due to the proximity of loop 2 (since $|\beta|<1$). This condition ensures efficient power coupling to loop 1 from external drive circuitry. The loop 1 reactance is also only weakly affected. Loop 1 can therefore excite significant RF magnetic field for purposes of magnetic resonance measurement, in a region defined by a field pattern similar to that produced by a single, completely isolated loop. By applying the principle of reciprocity, the same loop is therefore able to receive a signal generated in the same region. However, RF Interference (RFI) magnetic field having equal phase and magnitude across the two loops is significantly rejected, by virtue of the arranged phasing and magnitude of the scattered field. Numeric analysis of loop arrangements that include free space radiation effects yield similar RFI rejection attributes.

Thus, the provision of a passive loop, e.g. as described in preceding embodiments, can provide suppression of external electromagnetic interference in the main loop.

Example 2—The Role of the Passive Reflector

One role of the passive reflector is to reduce the RFI field impinging on loop 1 (the main loop). This function is achieved without the presence of loop 2. Loop 1 is placed in the region of reduced field, thereby lowering $\varepsilon_1$ and providing some RFI rejection.

Another role of the passive reflector is to reduce the mutual coupling between the main loop and the passive loop. The analysis above did not acknowledge that there may be practical restrictions in achieving the parameters chosen for RFI suppression. For example, in the analysis above we may assume that $r_2$=10 mΩ. It follows from the chosen parameter values that $jX_2$=−100 jmΩ and $j\omega M$=50 jmΩ. If the quality factor of the isolated loop 2 is say, 500, the reactance of the untuned loop is 5 jΩ. The required mutual reactance is therefore tiny compared to the reactance of the untuned loop. To achieve such a relatively small coupling between two similarly sized loops would normally involve an impractically large spatial separation, incompatible with the requirement for compactness. The passive reflector is interposed between loop 1 and loop 2. It is not a resonated structure and is not capable of significantly modifying the phase of scattered near field. Rather it acts to partially shield the field generated by one loop from the other by supporting eddy currents on the reflector surface. This optimises the value of M between loop 1 and loop 2 and allows the development of a compact spatial arrangement of loops.

Another role of the passive reflector is to boost the ratio $\alpha=\varepsilon_2/\varepsilon_1$ (thereby reducing $\beta$). A reduction in $\beta$ is favourable from the point of view of further reducing the reflected impedance occurring in loop 1 due to the proximity of loop 2 (as illustrated by equation 5). This provides for more efficient magnetic resonance signal coupling to loop 1.

Example 3—Passive Insert Function

Figure 8A:
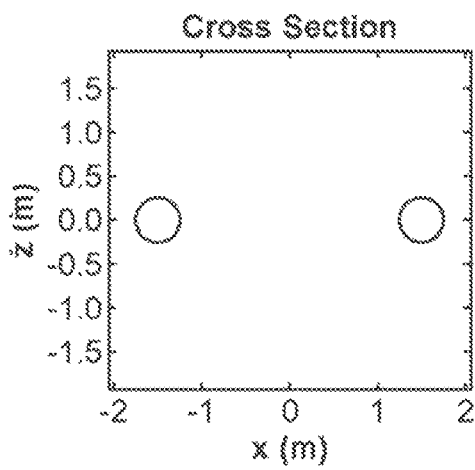
FIG. 8a shows a main loop cross section without an insert in the plane of the main loop.
Figure 8B:
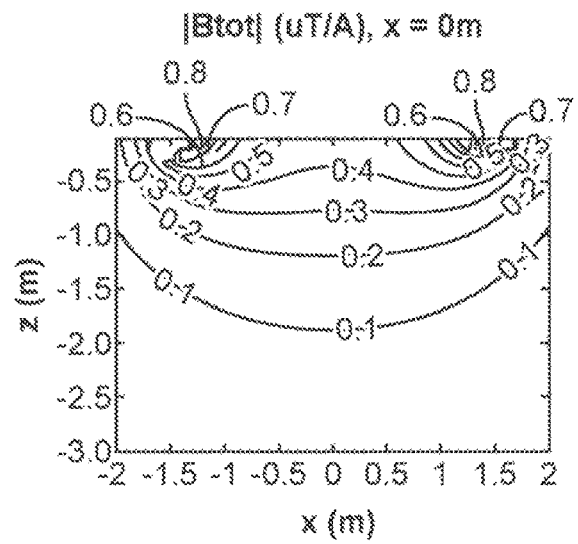
FIG. 8b shows corresponding calculated normalised RF magnetic field contours.
Figure 9A:
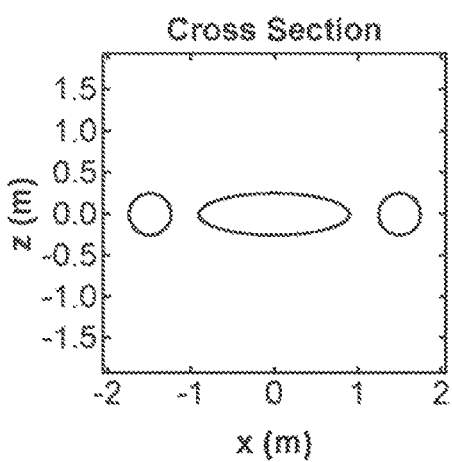
FIG. 9a shows a main loop cross section with an insert in the plane of the main loop.
Figure 9B:
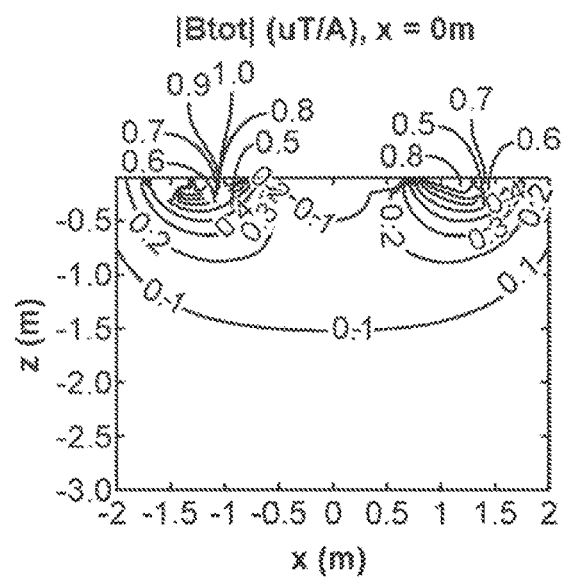
FIG. 9b shows corresponding calculated normalised RF magnetic field contours.

An insert, e.g. in accordance with the passive insert 306 described with respect to embodiments above, may be used for multiple purposes. For example, an insert reduces the RF field strength in the immediate vicinity of the main loop. This has the effect of reducing eddy currents in the ore very close to the loop, and therefore also the reflected resistance in the main loop. This creates the advantage that a significantly increased current can be driven in the main loop at the same available power level. FIGS. 8 and 9 compare the calculated field strength per unit current as a contour plot for a main loop without an insert (FIGS. 8a and 8b) and with an insert (FIGS. 9a and 9b). In FIG. 9b the insert is an oblate spheroid (see main loop cross section shown in FIG. 9a) placed in the plane of the main loop. The contours in FIG. 9b very close to the loop indicate significantly lower field strength. On the other hand, the field strength at distances far from the loop are much less affected by the insert. Depending on the severity of the eddy current losses, the increase in current afforded by the reduction in main loop resistance leads to an overall sensitivity advantage at larger distances from the sensor.

Figure 10:
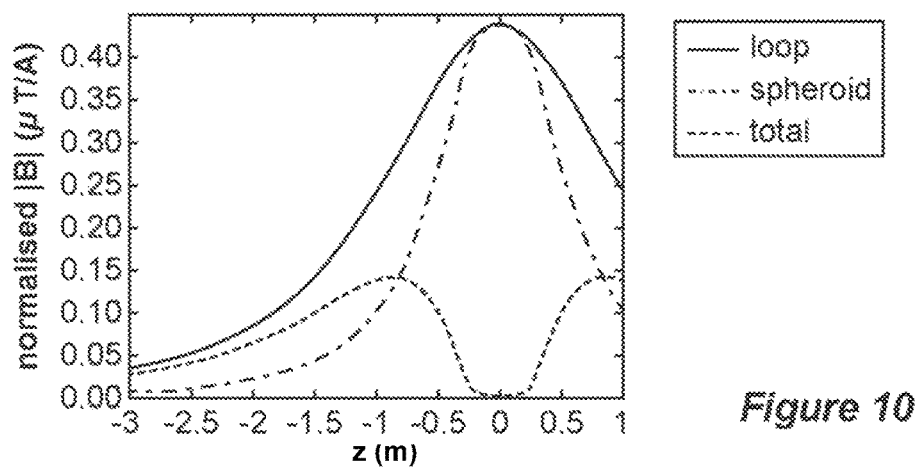
FIG. 10 shows normalised on-axis field per unit current for the main loop without insert of FIG. 8a (blue trace), and the main loop with insert of FIG. 9a (black trace), and the field generated by eddy currents on the insert surface (red trace)

An insert also reduces the sensitivity of the main loop at distances very close to the sensor, compared to distances further from the sensor, thereby "flattening" the sensor response with respect to depth. This is an advantage for providing higher homogeneity of the sensing across the ore half space. FIG. 10 shows a comparison plot between the normalised field (on axis) due to the main loop only (blue trace) and loop plus insert (black trace). The red trace is the field generated by eddy currents on the insert surface, that act to cancel field very close to the main field. The RF field very close to the main loop is preferentially reduced compared to the field far from the main loop. Because the sensitivity depends on the normalised RF field, an improvement in sensing homogeneity is achieved.

Example 4—Obtaining Uniform Spatial Sensitivity

Most sensing techniques, when applied for one-sided measurement applications, are constrained by the fact that the sensing field or flux decays away from the sensor, and where measurement response similarly decreases rapidly away from the sensor position, normally in at least a "$1/r^2$" fashion. While electromagnetic fields from loops also generally decay monotonically away from the loop aperture, the MR response profile can be made to peak some distance away from the sensor. This is because MR resonant responses have nonlinearity in the applied excitation field. There are various MR phenomena that can be exploited for profiling, including saturation, internal destructive interference, and variable magnetisation rotation, etc.

Figure 11:
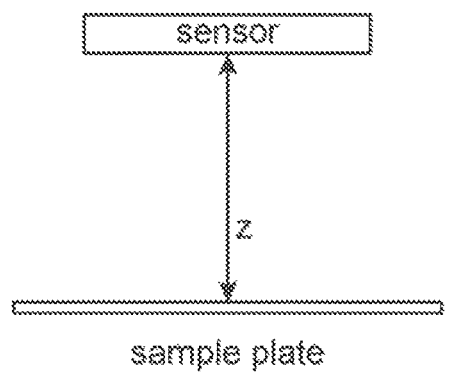
FIG. 11 shows an MR sensor suspended above a half space where a sample comprising a thin circular disc, in a plane parallel to the sensor face, may be positioned at different displacements (z) from the sensor.

Experiments have been performed to demonstrate methods for sensitivity profiling. FIG. 11 shows an MR sensor suspended above a half space where a sample comprising a thin circular disc, in a plane parallel to the sensor face, may be positioned at different displacements from the sensor. The disc was used to mimic a thin layer of mineralisation in the half space beneath the sensor. The separation of the disc and the sensor was varied to characterise the response of the sensor with respect to mineral depth, for different MR pulse sequences and signal analysis methods (masks). For each type of sequence and signal analysis method, a different relationship between sensitivity and sample depth can be obtained. These relationships are herein called "sensitivity profiles". The experiments described above represent a calibration procedure in which various sensitivity profiles are generated prior to their use in ore half-space measurement.

Figure 12A:
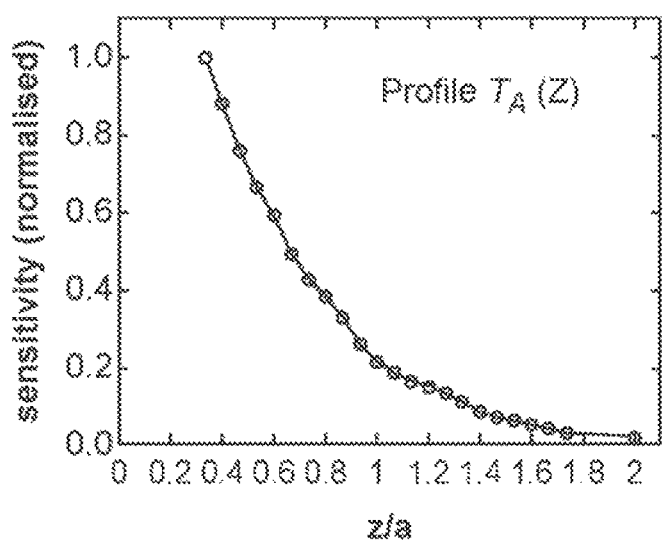
FIGS. 12a-c show three different sensitivity profiles obtained for three different pulse sequences and analysis methods.
Figure 12B:
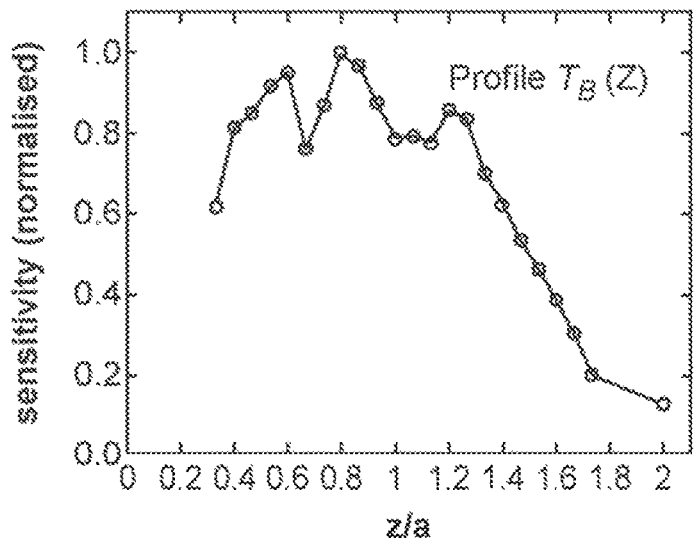
Figure 12C:
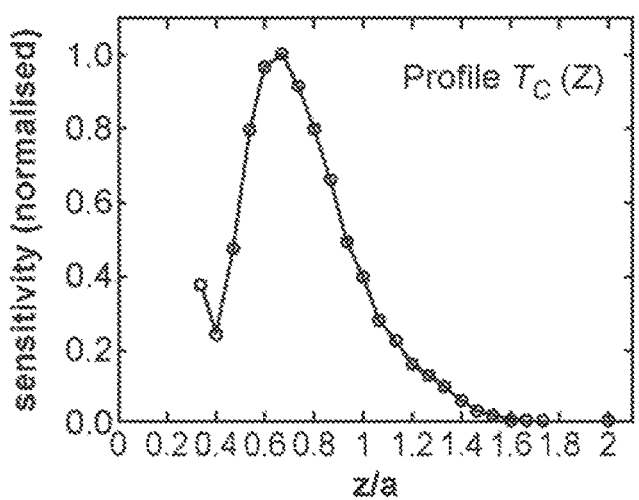

FIGS. 12a-c shows three different sensitivity profiles obtained for three different pulse sequences and analysis methods (masks). Profile A (FIG. 12a) results from the analysis of MR signal power at early times during a free induction decay (FID) that is generated by a specific pulse sequence (in this case a single long pulse). Profile B (FIG. 12b) results from analysis of the same type of FID at later time periods.

Figure 13A:
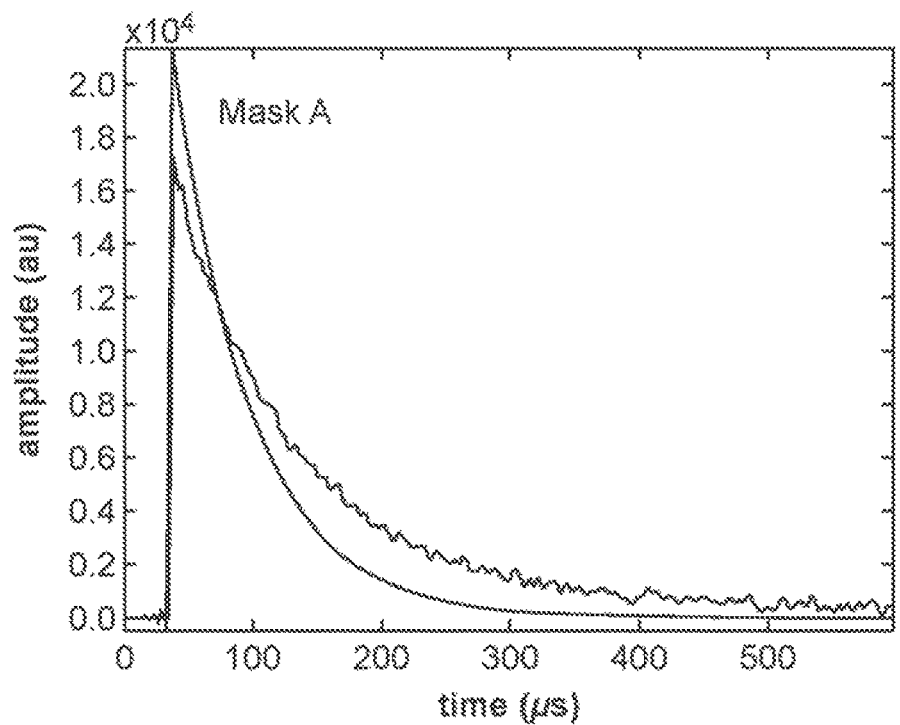
FIGS. 13a-b show masks used to extract signal power at different times in a FID waveform corresponding to (a) early-time analysis, and (b) late time analysis.
Figure 13B:
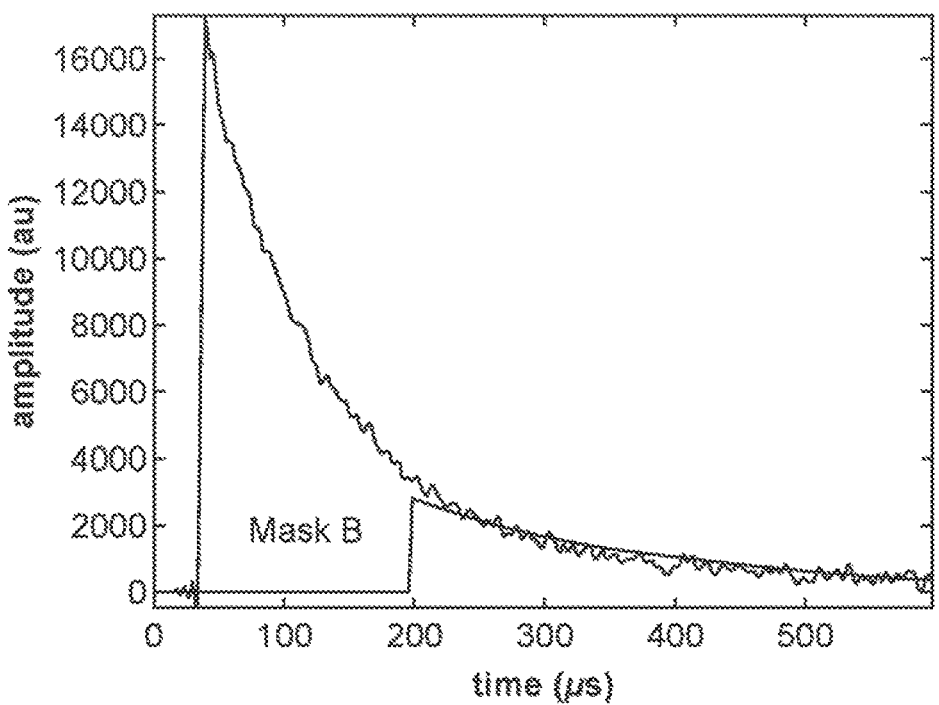

FIGS. 13a and 13b show the masking approach used to generate the sensitivity profiles. Masks have been applied to specific time-domains of the signal to extract the specific portion of signal power occurring over those periods. In this example, masks are used to extract signal power at different times in the FID waveform corresponding to early-time analysis (FIG. 13a), and late time analysis (FIG. 13b). Profile C (shown in FIG. 12c) results from analysis of magnetic resonance responses derived from shorter pulse lengths. A number of different sensitivity profiles may be developed in an actual ore measurement, as the MR measurement parameters can be dynamically varied in real time to interleave the generation of specific sensitivity profiles in the normal course of operation.

It is noted that relatively constant sensitivity with depth is achievable by simply using the pulse and analysis parameters corresponding to Profile A. This demonstrates that, for this configuration, the MR measurement is not "swamped" by grade close to the surface, i.e., the measurement is not strongly biased according to upper zone grade.

The sensitivity profiles in FIGS. 12a-c also allow the development of composite sensitivity profiles, of a desired shape, by linear combination of the available sensitivity profiles. The sensitivity profiles, loosely speaking, form a "basis set"; each sensitivity profile can be summed in a weighted linear combination to reproduce a new sensitivity profile that is designed to overlap strongly with the specified measurement zones.

The weighting procedure is performed as follows. Each MR measurement configuration provides a single waveform for the entire half space under the sensor. The waveform for each configuration is analysed using the signal masks to extract one or more sensitivity profile "weightings". For example, for the long pulse configuration, the early and late-time signal power and is analysed to provide two numbers ($S_A$ and $S_B$ respectively) that estimate the weighting of each sensitivity profile pattern in the half space. In the example explored here, a third sensitivity profile strength $S_C$ is also derived from a second MR measurement configuration (short pulse configuration). Each sensitivity profile weighting is normalised to the known calibrated weighting corresponding to a uniform ore grade of definite value.

Therefore the sensitivity profile strengths carry information relating to both profile and quantitative grade value.

Once the sensitivity profile weightings are determined, they can be used to weight the corresponding sensitivity profile to estimate the shape of the grade profile in the specified zone in the half space. Multiple sensitivity profiles can be employed in order to optimize a flat response with depth, or alternatively, setup sensitivity profile combinations that are preferentially weighted in specific zones. The later method allows the profiling of grade with depth.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An apparatus for the measurement of ore in mine haul vehicles, the apparatus comprising:
   a portal, defining a portal zone, wherein a haul vehicle carrying ore is positionable in or movable through the portal zone,
   at least one magnetic resonance (MR) sensor positioned in the portal, the magnetic resonance sensor comprising:
   a main loop positionable in the portal zone above or on an ore burden carried by the haul vehicle,
   a drive loop located above the main loop and electrically isolated from and magnetically coupled to the main loop,
   wherein a radio frequency (RF) transmitter is couplable to a feed terminal of the drive loop to drive an RF drive current in the drive loop and a radio frequency receiver is couplable to the drive loop to monitor an RF response current in the drive loop;
   the apparatus further comprising:
   a magnetic resonance sensor control system configured to control at least one of:
   positioning the at least one MR sensor relative to the portal zone and/or the ore burden;
   positioning the main loop relative to the drive loop;
   electromagnetic suppression characteristics of the at least one MR sensor; and/or
   sensitivity of the at least one MR sensor as a function of distance of the sensor from the ore burden.

2. The apparatus of claim 1, wherein the main loop comprises a plurality of conductive segments and capacitors positioned between the conductive segments.

3. The apparatus of claim 2, wherein the capacitors are evenly spaced along the main loop and capacitance of each capacitor is substantially equal.

4. The apparatus of claim 2, wherein the capacitance of at least one of the capacitors of the main loop is adjustable.

5. The apparatus of claim 4, wherein the sensor control system is configured to adjust the capacitance of at least one of the capacitors of the main loop.

6. The apparatus of claim 5, further comprising an impedance monitor to monitor reactive impedance at the feed terminal of the drive loop, wherein the sensor control system adjusts the capacitance based on the monitored reactive impedance.

7. The apparatus of claim 6, wherein the sensor control system is configured to adjust the capacitance so that the reactive impedance at the feed terminal of the drive loop is at a target reactive impedance.

8. The apparatus of claim 2, wherein the conductive segments and capacitors of the main loop extend along a looped path and, in cross-section, in a plane perpendicular to the looped path, the conductive segments have a non-circular cross-sectional shape.

9. The apparatus of claim 8, wherein the non-circular shape is:
   a shape having a convex border and an opposing concave border; or
   a shape having a convex border and an opposing concave border wherein the convex border is at a radially outer side of the main loop and the concave border is at a radially inner side of the main loop; or
   a crescent shape, a kidney-shape, or a crescent shape formed by two-intersecting ellipses.

10. The apparatus of claim 1, wherein the sensor control system is configured to adjust:
    a position and/or orientation of the at least one MR sensor relative to the ore burden; and/or
    a position and/or orientation of the drive loop relative to the main loop.

11. The apparatus of claim 10, further comprising an impedance monitor to monitor resistive impedance at the feed terminal of the drive loop, wherein the sensor control system adjusts:
    the position and/or orientation of the at least one MR sensor relative to the ore burden based on the monitored resistive impedance; and/or
    the position and/or orientation of the drive loop relative to the main loop based on the monitored resistive impedance.

12. The apparatus of claim 11, wherein the sensor control system adjusts the position and/or orientation so that the resistive impedance at the feed terminal of the drive loop is at a target resistive impedance.

13. The apparatus of claim 12, wherein the sensor control system adjusts the position and/or orientation of the at least one sensor relative to the ore burden such that the resistive impedance at the feed terminal of the drive loop is within a predetermined resistive impedance range and subsequently adjusts the position and/or orientation of the drive loop relative to the main loop such that the resistive impedance at the feed terminal of the drive loop is at the target resistive impedance.

14. The apparatus of claim 10, comprising a displacement monitor to monitor a displacement between the at least one MR sensor and the ore burden.

15. The apparatus of claim 14, wherein the sensor control system adjusts the position and/or orientation based on the monitored displacement.

16. The apparatus of claim 15, wherein the sensor control system adjusts the position and/or orientation based on the monitored displacement to maintain a fixed separation between the ore burden and the main loop.

17. The apparatus of claim 1 further comprising a passive loop located above the main loop or in the plane of the main loop, the passive loop suppressing external electromagnetic interface in the main loop.

18. The apparatus of claim 17, further comprising a reflector positioned above the main loop, the reflector being configured to reduce radiation and magnetic near field in an upward direction from the ore burden, wherein the reflector is located between the main loop and the passive loop.

19. The apparatus of claim 17, wherein the passive loop has a capacitive lump impedance that is adjustable by the sensor control system to optimise suppression of external electromagnetic interface in the main loop.

20. The apparatus of claim 19 further comprising a noise monitor to monitor RF noise voltage at the feed terminal of the drive loop, wherein the sensor control system is configured to adjust the capacitive lump impedance of the passive loop based on the monitored RF noise voltage to minimise the RF noise voltage at the feed terminal of the drive loop.

21. The apparatus of claim 1 further comprising a resistive loop magnetically coupled to the main loop and terminated with a resistance, wherein the sensor control system is configured to adjust an orientation of the resistive loop relative to the main loop.

22. The apparatus of claim 21, comprising an impedance monitor to monitor resistive impedance at the feed terminal of the drive loop and wherein the sensor control system is configured to adjust the orientation of the resistive loop relative to the main loop based on the monitored resistive impedance such that the resistive impedance at the feed terminal of the drive loop is at the target resistive impedance.

23. The apparatus of claim 1 further comprising an insert that is positioned radially inside of the main loop, in a plain of the main loop, wherein the insert is an oblate spheroid.

24. The apparatus of claim 1, wherein the haul vehicle is a truck, a Load-Haul-Dump (LHD) vehicle, a skip, a wagon or a cart.

25. The apparatus of claim 1 further comprising a portal control system, wherein the portal control system is configured to control movement of the haul vehicle through the portal zone of the portal.

26. The apparatus of claim 1, wherein to control the sensitivity of the at least one MR sensor as a function of distance of the sensor from the ore burden, the sensor control system is configured to:
 control application of at least one RF pulse sequence to the MR sensor and use at least one corresponding analysis method to analyse an MR response signal from the ore burden, wherein the at least one RF pulse sequence and its corresponding analysis method have a corresponding predetermined sensitivity profile,
 use the analysis of the MR response signal to measure a corresponding sensitivity profile weighting; and
 use the sensitivity profile weighting to estimate the mineral concentration in the ore burden as a function of depth.

27. The apparatus of claim 1, wherein to control the sensitivity of the at least one MR sensor as a function of distance of the sensor from the ore burden, the sensor control system is configured to:
 control application of a first RF pulse sequence to the MR sensor and use a corresponding first analysis method to analyse a first MR response signal from the ore burden, wherein the first RF pulse sequence and the first corresponding analysis method have a corresponding first predetermined sensitivity profile,
 control application of one or more further RF pulse sequences to the MR sensor and use one or more corresponding further analysis methods to analyse one or more further MR response signals from the ore burden, wherein the one or more further RF pulse sequences and the one or more further corresponding analysis methods each have corresponding further predetermined sensitivity profiles,
 use the analysis of the first and further MR response signals to measure corresponding first and further sensitivity profile weightings;
 sum the first and further sensitivity profile weightings to create a preferred spatial sensitivity profile weighting; and
 use the preferred sensitivity profile weighting to estimate the mineral concentration in the ore burden as a function of depth.

28. A method of measuring ore in mine haul vehicles using the apparatus of claim 1.

* * * * *